(12) United States Patent
Sturm et al.

(10) Patent No.: US 8,148,690 B2
(45) Date of Patent: Apr. 3, 2012

(54) METHOD AND APPARATUS FOR ON-LINE WEB PROPERTY MEASUREMENT

(75) Inventors: Steven P. Sturm, Dublin, OH (US); Michael S. O'Hora, Dundalk (IE); Rodney D. Maxson, Supply, VA (US)

(73) Assignee: ABB, Ltd., Dublin (IE)

(*) Notice: Subject to any disclaimer, the term of this patent is extended or adjusted under 35 U.S.C. 154(b) by 163 days.

(21) Appl. No.: 12/566,180

(22) Filed: Sep. 24, 2009

(65) Prior Publication Data

US 2011/0068261 A1 Mar. 24, 2011

(51) Int. Cl.
*G01N 21/86* (2006.01)

(52) U.S. Cl. .................................. 250/339.07
(58) Field of Classification Search .............. 250/339.07
See application file for complete search history.

(56) References Cited

U.S. PATENT DOCUMENTS

| | | | |
|---|---|---|---|
| 4,479,055 A | 10/1984 | Perten | |
| 4,577,104 A | 3/1986 | Sturm | |
| 4,812,665 A | 3/1989 | Puumalainen et al. | |
| 4,904,088 A | 2/1990 | Blazek et al. | |
| 5,124,552 A | 6/1992 | Anderson | |
| 5,563,809 A | 10/1996 | Williams et al. | |
| 6,254,726 B1 | 7/2001 | Steiner et al. | |
| 6,960,769 B2* | 11/2005 | Burk et al. | 250/339.07 |
| 7,494,567 B2 | 2/2009 | Haran | |
| 2004/0036024 A1 | 2/2004 | Skelton | |
| 2004/0065829 A1 | 4/2004 | Burk et al. | |
| 2005/0135766 A1 | 6/2005 | Cianciotto et al. | |
| 2006/0152731 A1 | 7/2006 | Maentele et al. | |
| 2006/0251376 A1 | 11/2006 | Cianciotto et al. | |
| 2006/0256449 A1 | 11/2006 | Cianciotto et al. | |
| 2006/0285815 A1 | 12/2006 | Cianciotto et al. | |
| 2009/0128799 A1 | 5/2009 | MacHattie et al. | |

FOREIGN PATENT DOCUMENTS

| | | |
|---|---|---|
| CN | 1800825 A | 7/2006 |
| DE | 10004612 A1 | 5/2001 |
| EP | 0453797 A2 | 10/1991 |
| JP | 1032152 A | 2/1989 |
| JP | 1167637 A | 7/1989 |
| JP | 2147838 A | 6/1990 |
| JP | 3015740 A | 1/1991 |
| JP | 3105236 A | 5/1991 |
| JP | 4034342 A | 2/1992 |
| JP | 6058872 A | 3/1994 |

(Continued)

OTHER PUBLICATIONS

Voith Moisture Sensor; Sensor for Moisture Measurement; available May 15, 2009.

(Continued)

*Primary Examiner* — David Porta
*Assistant Examiner* — Christine Sung
(74) *Attorney, Agent, or Firm* — Stevens & Showalter LLP

(57) ABSTRACT

Web measurement system monitors properties of a web during manufacture without chopping measuring radiation during web measurement. A single chop is performed at each sheet edge or every $n^{th}$ sheet edge to measure edge temperature and edge thermal radiation for correction for Planckian radiation. Correction factors, including Planckian radiation correction factors, are derived for each point in a web profile. The measuring system also enables derivation of correction factors during operation in a single point and similar machine operating modes.

19 Claims, 7 Drawing Sheets

FOREIGN PATENT DOCUMENTS

| | | | |
|---|---|---|---|
| JP | 6294736 | A | 10/1994 |
| JP | 7260680 | A | 10/1995 |
| JP | 11173981 | A | 7/1999 |
| JP | 11237377 | A | 8/1999 |
| JP | 2004361149 | A | 12/2004 |
| JP | 2005164303 | A | 6/2005 |
| WO | 0159435 | A1 | 8/2001 |
| WO | 2007038495 | A2 | 4/2007 |

OTHER PUBLICATIONS

Schulze, Cornelia; International Search Report and Written Opinion; Mar. 11, 2011; pp. 1-9; International Application No. PCT/IB2010/002440; European Patent Office; Rijswijk Netherlands.

* cited by examiner

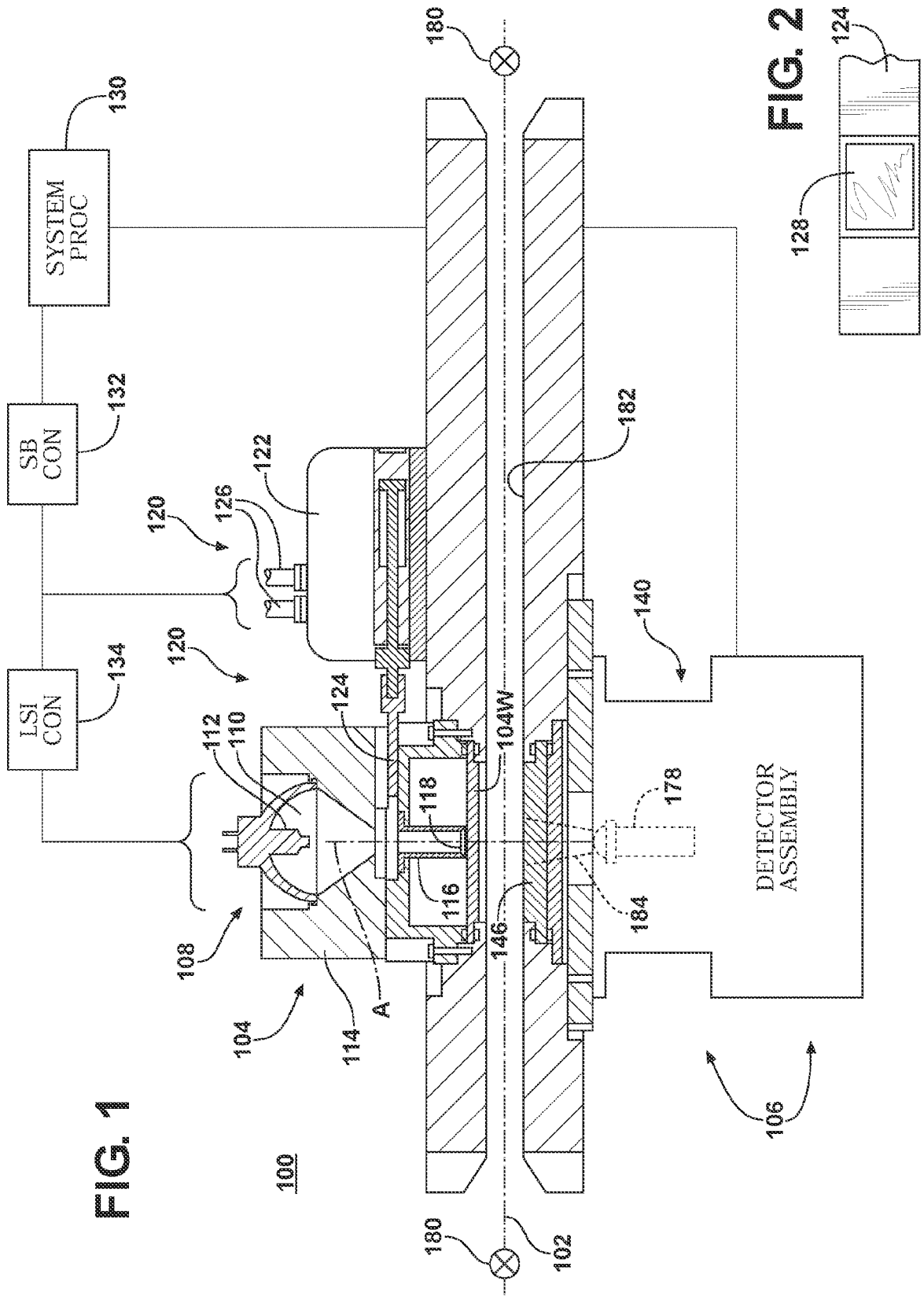

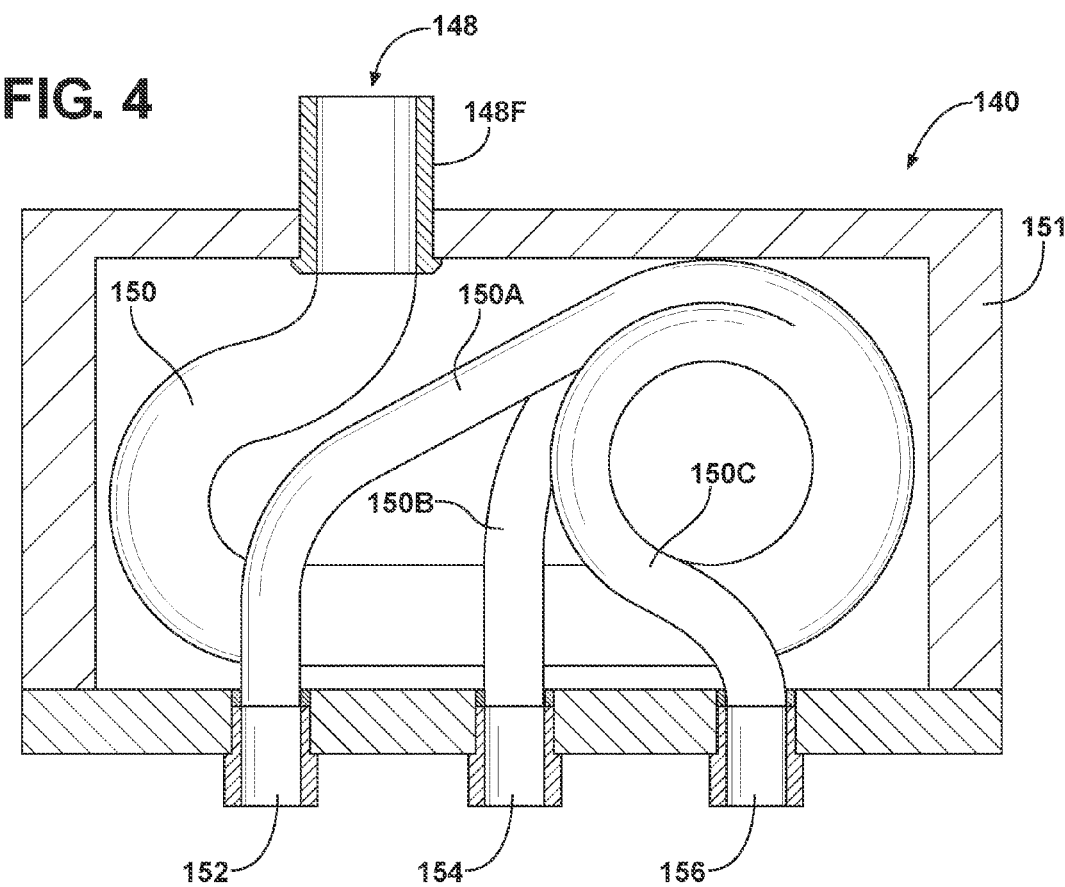
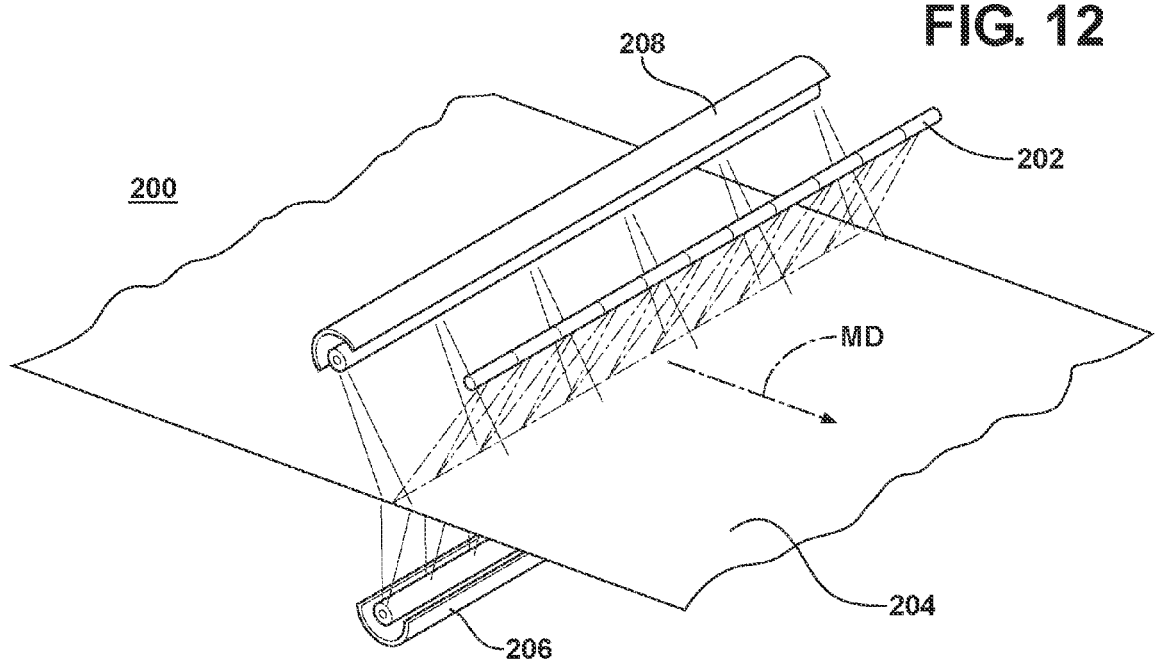

METHOD AND APPARATUS FOR ON-LINE WEB PROPERTY MEASUREMENT

FIELD OF THE INVENTION

The invention of the present application relates to a method and apparatus for on-line web property measurement including a signal normalization method and apparatus for utilizing the method. The method and apparatus will be described with reference to measuring properties of a web of paper as it is being manufactured for which it is initially being used. However, it will be apparent that the method and apparatus are applicable to other web manufacturing processes.

BACKGROUND OF THE INVENTION

During the manufacture of webs of flat sheet materials, such as paper, plastic films, textiles and the like, the webs are monitored by devices, which may be referred to herein as detectors or sensors interchangeably, that feedback information used to control manufacturing. Manual or automated process control systems may use this information. Sensors used in process control systems need to accurately measure properties of a quickly moving, fluttering web, while operating in a high humidity, dirty, hot and/or wet environment. Such sensors usually mount on measurement platforms that scan the sensors in a cross machine direction (CD) as the process web moves relatively rapidly in a machine direction (MD).

Infrared spectroscopic sensors are common monitoring devices for such control systems. These sensors measure the absorption of infrared radiation at specific wavelength bands, indicating a specific property's presence and/or magnitude. Specific characteristics that the sensors may measure include properties such as water, polymers, coating minerals, cellulose and other components of a web. A common application is the measurement of the fraction of water by weight (percent moisture) in a moving paper web during manufacturing.

The infrared spectroscopic sensor measurements utilize the differential absorption of various wavelength bands in the near infrared region, generally 0.75 µm to 10.0 µm, by water and other components of the web. Process controllers compare measurements of the transmission and/or reflection of infrared energy at one or more reference wavelengths to measurements of the transmission and/or reflection at one or more absorption wavelengths. The reference wavelengths are selected for a relatively low absorption coefficient by as many of the components of the web as possible, and the absorption wavelengths are selected for a relatively high absorption coefficient. A number of different wavelength measurements may be used to determine and/or reject other interfering parameters, such as the mean optical path length through the web as a result of optical scattering.

The infrared radiation sensors, such as lead sulfide (PbS), lead selenide (PbSe) or Indium Gallium Arsenide (InGaAs) sensors, generally measure infrared energy in several spectral bands, making all measurements simultaneously with the measurements being representative of the same area of the moving process web. Simultaneous measurement generally requires multiple, spatially separated sensors, each of which detects infrared energy at one of the spectral bands of interest. Since the properties of the web that affect the various infrared wavelengths can vary over short distances on the web, any differences in the web areas presented to the sensors may result in measurement error. Simply placing the individual sensors proximate to each other is generally inadequate to meet accuracy requirements. The signals from these sensors may be mathematically combined to develop measurements of interest.

Indium Gallium Arsenide (InGaAs) sensors are generally preferred since lead salt sensors are more sensitive to temperature and thus require more frequent normalization to correct errors produced by temperature drift and sensor dark current. Almost all currently available web property measuring systems normalize sensor signals by using continuous chopping devices such as filter wheels, tuning forks, rotating blades, shutters or the like. Traditional continuous chopping reduces the measurement signal. At best, a beam having a sinusoidal chop has half the average energy of a beam that is not chopped.

SUMMARY OF THE INVENTION

The on-line web property measurement system of the present application enables properties of a web of material to be monitored on-line during manufacture without chopping a measuring radiation beam during web measurement. Rather than using conventional continuous chopping, which interrupts the measuring radiation beam each time the chopper closes, in the measurement system of the present application, a single chop is performed at each edge of sheet or every $n^{th}$ edge of sheet. During edge of sheet chops, edge temperature data and edge thermal radiation data are measured and used to correct for web thermal radiation, i.e., Planckian radiation, and electronic offset drift in each measurement channel of the system. As the web is scanned, at least one pyrometer on a scanning head package measures a web temperature profile, i.e., the temperature at consecutive points across the web. From data measured at an edge of sheet, correction factors, including correction for Planckian radiation, are derived for each point in the web profile. When the correction factors are applied, the data measured in each channel accurately represents characteristics of the web that are to be measured.

In addition to performing chops at edges of the sheet, which edge of sheet chops are performed during normal sheet production and scanning measurements, the measuring system of the present application also enables derivation of correction factors during measurements taken at a single point in the web cross direction when using either a scanning measurement system stopped at the single point or a non-scanning measurement system.

In accordance with one aspect of the present invention, a method for measuring at least one property of a web of material as the web is being manufactured and is moving in a machine direction (MD) by scanning measurement apparatus back and forth across the web in a cross-machine direction (CD), the measuring apparatus comprising a source of radiation appropriate for measuring the at least one property that is directed toward the web and at least first and second sensors that receive measuring radiation from the web comprises: receiving radiation representative of the at least one property of the web at consecutive points across the web; measuring temperature at the consecutive points across the web; interrupting the measuring radiation at an edge of the web; sensing radiation at the edge of the web while the measuring radiation is interrupted; measuring temperature of the edge of the web; developing correction factors for the at least one property from the web edge temperature and the measured temperatures of the consecutive points for each of the consecutive points across the web; and, applying the correction factors at each of the consecutive points across the web to correct for Planckian radiation contained in radiation representative of the at least one property of the web received at the consecutive points across the web.

In accordance with another aspect of the present invention, apparatus for measuring at least one property of a web of material as the web is being manufactured and is moving in a machine direction (MD) by scanning the measurement apparatus back and forth across the web in a cross-machine direction (CD) comprises a source of measuring radiation appropriate for measuring the at least one property, the measuring radiation being directed toward the web. At least first and second sensors receive radiation from the web and generate signals representative of the radiation. At least one pyrometer measures the temperature of the web. A shutter mechanism interrupts the source of measuring radiation when the sensor is positioned on an edge of the web wherein the sensor generates signals in response to measuring radiation representative of the at least one property and Planckian radiation when the source of measuring radiation is uninterrupted for each of the consecutive points extending across the web between edges of the web and the sensor generates signals in response to Planckian radiation for at least one of the edges of the web while the source of measuring radiation is interrupted, and the pyrometer measures a temperature for each of the consecutive points extending across the web and for at least one of the edges of the web. A controller develops correction factors for the at least one property for each of the consecutive points across the web from a measured edge temperature and the measured temperatures of each of the consecutive points across the web, and applies the correction factors for each of the consecutive points across the web to correct for Planckian radiation contained in radiation sensed for each of the consecutive points across the web.

In accordance with yet another aspect of the present invention, apparatus for measuring at least one property of a web of material as the web is being manufactured and is moving in a machine direction (MD) by scanning the measurement apparatus back and forth across the web in a cross-machine direction (CD) comprises a source of measuring radiation appropriate for measuring the at least one property, the measuring radiation being directed toward a first side of the web. Beam splitting apparatus receives radiation from a second side of the web opposite to the first side, the beam splitting apparatus having a radiation input port directed toward an area of the web irradiated by the measuring radiation and at least a first output port and a second output port. A first sensor receives radiation from the first output port of the beam splitting apparatus and generates signals representative of received radiation. A second sensor receives radiation from the second output port of the beam splitting apparatus and generates signals representative of received radiation. A pyrometer measures a temperature of the web. A shutter mechanism interrupts the source of measuring radiation when the sensor is positioned on an edge of the web wherein the first and second sensors generate signals in response to measuring radiation and Planckian radiation when the source of measuring radiation is uninterrupted for each of consecutive points extending across the web between edges of the web and the first and second sensors generate signals in response to Planckian radiation for at least one of the edges of the web while the source of measuring radiation is interrupted, and the pyrometer measures a temperature for each of the consecutive points extending across the web and for at least one of the edges of the web. A controller develops correction factors for the at least one property for each of the consecutive points across the web from a measured edge temperature and measured temperatures of each of the consecutive points across the web, and applies the correction factors for each of the consecutive points across the web to correct for Planckian radiation contained in radiation sensed for each of the consecutive points extending across the web between the edges of the web.

In accordance with still another aspect of the present invention, a method for measuring at least one property of a web of material as the web is being manufactured and is moving in a machine direction (MD), the measuring apparatus comprising a source of radiation appropriate for measuring the at least one property that is directed toward the web and at least first and second sensors that receive measuring radiation from the web, the method comprising: receiving radiation representative of the at least one property of the web from at least one point in the cross direction (CD) of the web; measuring temperature at the at least one point in the CD of the web; interrupting the measuring radiation; sensing radiation received from the web while the measuring radiation is interrupted; measuring temperature of the web while the measuring radiation is interrupted; developing correction factors for the at least one property from the temperature measured while the measuring radiation is interrupted and the measured temperatures of the at least one point of the web; and applying the correction factors at the at least one point of the web to correct for Planckian radiation contained in radiation representative of the at least one property of the web received at the at least one point of the web.

BRIEF DESCRIPTION OF THE DRAWINGS

The benefits and advantages of the invention of the present application will become apparent to those skilled in the art to which the invention relates from the subsequent description of the illustrated embodiments and the appended claims, taken in conjunction with the accompanying drawings, in which:

FIG. 1 is a partially sectioned side view of apparatus in accordance with the invention of the present application;

FIG. 2 is a plan view of a shutter blade usable in the apparatus of FIG. 1;

FIGS. 4 and 5 are schematic views of a fiber optic beam splitter that serves as both a light distributor and homogenizer for the invention of the present application;

FIG. 12 schematically illustrates a non-scanning measurement system utilizing the invention of the present application and including an array of fixed sensors that extend across an entire web being manufactured.

DETAILED DESCRIPTION OF THE INVENTION

Figure 3:
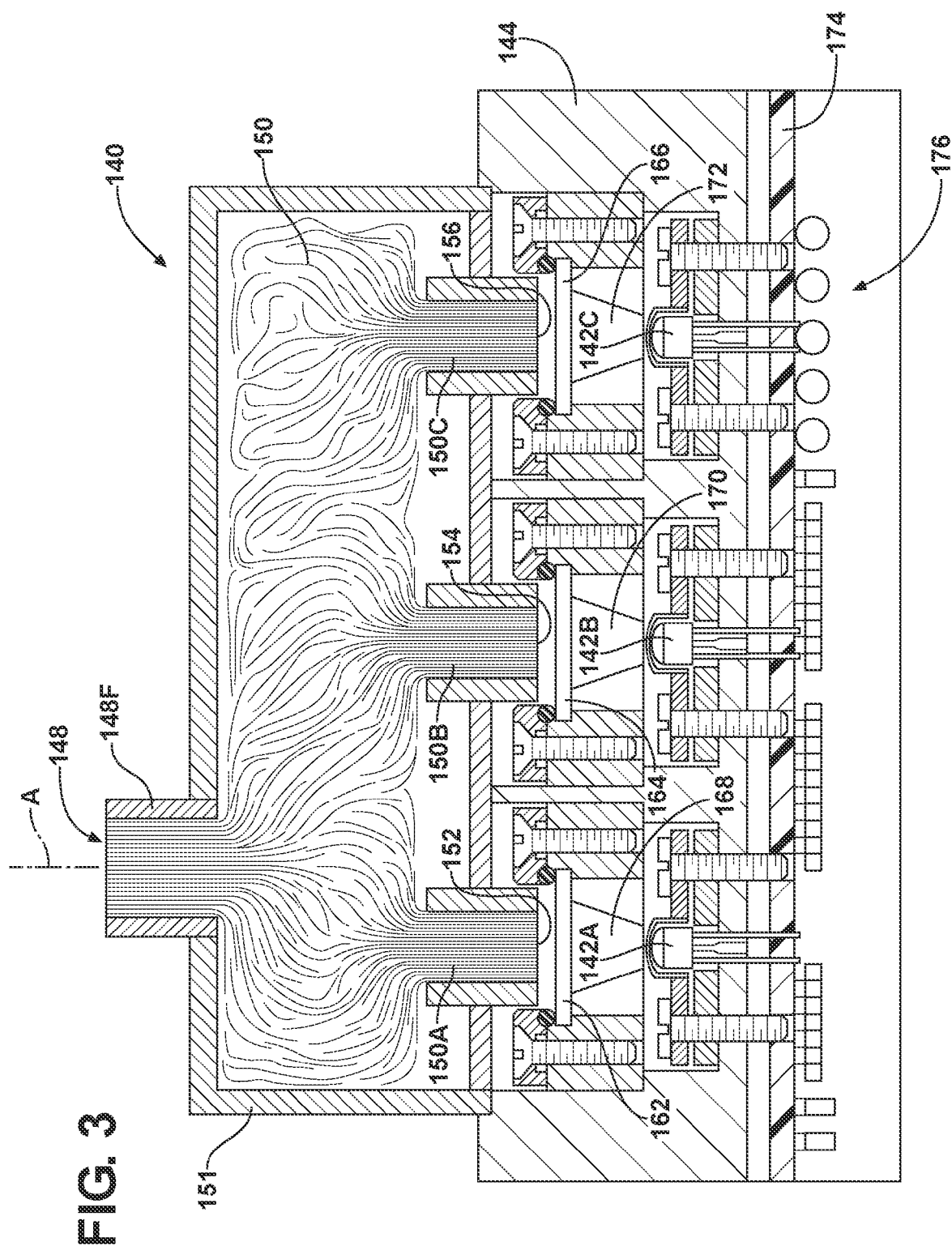
FIG. 3 is a partially sectioned side view of a detector assembly shown in FIG. 1.

The invention of the present application is directed to improving the signal to noise (S/N) ratio and bandwidth of an on-line web measurement system. By improving the S/N ratio and bandwidth, the system is able to measure short term material property variations with high precision on a fast moving web.

Typical on-line measuring systems use beam choppers that block measuring radiation while the measuring systems are over portions of the web that are to be measured and web material properties cannot be measured during the time that the beam is blocked. Beam chopping schemes may use tuning forks, spinning wheels with teeth or holes, or the like. Beam chopping typically reduces the total radiation flux by 50% or more. The invention of the present application enables on-line infrared material property measurements without chopping during measurements performed during normal web production operations. Instead, chops are normally performed at sheet edges where a scanner reverses direction for repeated scans of a web being manufactured. Accordingly, more radiation flux is available during web measurement operations resulting in an improvement S/N ratio.

Beam chopping acts as a sampling system and therefore sets limits on measurement bandwidth. Current state-of-the-art beam choppers chop or interrupt the beam between 200 and 1000 times per second. Therefore, the Nyquist frequency is 100 to 500 Hz, which is the upper bound of the highest frequency measurement data can unambiguously represent. Non-chopped measurements using the invention of the present application provide discrete sampling of at least 5000 samples per second to provide an upper bound on the highest frequency the data can unambiguously represent of at least 2500 Hz. Sampling rates faster than 5000 samples per second are also contemplated for operation of the invention of the present application.

Referring now to the drawings, in which like-referenced characters indicate corresponding elements throughout the several views, FIG. 1 shows an embodiment of an infrared measuring apparatus 100 in accordance with the present invention for measuring characteristics or properties of a web product. While the present invention is generally applicable to measurement of a variety of web products, the present invention will be described herein with reference to measurement of a paper web 102 as it is being manufactured. The infrared measuring apparatus 100 includes a source assembly 104 and a detector assembly 106.

The source assembly 104 utilizes a broad bandwidth or white light source (hereinafter referred to as the light source 108) that has a light intensity controlled by the level of voltage and/or current applied to the light source 108. The light source 108 comprises a focused projection lamp, such as a tungsten halogen gold plated reflector lamp having a gold plated ellipsoidal reflector 110 and a bulb or lamp 112 with a tungsten filament surrounded by halogen gas. In a working embodiment, the light source 108 was a commercially available Gilway Technical Lamp (now International Light Technologies) part number L6408-G which is voltage controlled. The source assembly 104 also includes a source window 104W made from borosilicate glass, obtained from Schott A G of Jena, Germany, was used in a working embodiment, and is aluminized on the interior surface to form an annular reflector AR shown in FIG. 6.

Since the detector assembly 106 detects light in and near the 2 μm wavelength range, the voltage provided to the light source 108 may be reduced below a design voltage to cool the lamp and shift its emission curve away from the visible spectrum, from a design "color temperature" of about 3500K to a target temperature of about 2600K. Thus, the light source 108 preferably emits primarily infrared light radiation. The light source 108 preferably emits a high energy density broadband light including infrared and near infrared wavelengths of interest onto a focal spot of about one centimeter diameter at a controlled focal distance from an edge of the reflector 110. The light source 108 may be air-cooled using channels in an aluminum lamp block 114 or otherwise cooled to increase lamp life and to reduce heating effects on the measuring system. The source assembly 104 may also include a light pipe 116 to direct the light from the light source 108. The light pipe 116 is cylindrical in shape and has a reflective inner surface. Additionally, a diffuser 118 may be mounted at the end of the light pipe 116 farthest from the light source 108 to reduce sensitivity to moisture in dust residing on the window 104W, if desired.

The source assembly 104 also includes a shutter system 120 having a shutter controller 122 and a shutter blade 124. The illustrated shutter controller 122 is pneumatically operated through air tubes 126; however, the controller 122 can also be driven electrically or otherwise. The controller 122 quickly blocks (closed position) and unblocks (open position) the beam from the light source 108. In addition to blocking and unblocking the light source 108, the controller 122 can have an optional third position that presents a sample to the measurement system. For example, as shown in FIG. 2, a location for a replaceable standardization sample 128 may be included in the shutter blade 124.

The shutter blade 124 is preferably constructed of a metal, for example, titanium, aluminum or other suitable metal. The shutter blade 124 preferably is polished on a side facing away from the light source 108 to reduce its emissivity and includes a light absorbing coating on the side facing the light source 108. The light absorbing coating may be a flat black paint and may aid in conducting heat resulting from blocking the light source 108 away from the shutter blade 124.

The measuring apparatus 100 is controlled by a system processor 130 that controls the shutter system 120 through a pneumatic shutter blade controller 132, and controls the light source 108 through a light source intensity controller 134. The source assembly 104 may also include transducers (not shown) for monitoring temperature, power status, and other conditions of the source assembly 104.

Referring to FIGS. 1 and 3, the detector assembly 106 includes beam splitting apparatus comprising a fiber optic beam splitter 140 that serves as both a light distributor and homogenizer as more fully described below. The illustrated detector assembly 106 has the capacity of housing three light detector elements 142A, 142B, 142C (which may be identified herein generally by the reference numeral 142), within a detector housing 144. The detector housing 144 also houses electronic measurement printed circuit boards, interference filters, conical light collectors, etc. for operation of the measuring apparatus 100.

Of course, housing assemblies accommodating more than three light detector elements or fewer than three light detector elements may be used in the invention of the present application. For example, an additional detector element may be used for synchronization, i.e., it may serve as a "synch" detector for processing signals generated by the other detector elements as taught in U.S. Pat. No. 6,960,769 which is assigned to the assignee of the present application and is incorporated herein by reference in its entirety. The detector elements 142 are preferably Indium Gallium Arsenide (InGaAs) detectors but other detector technologies may be used depending on desired properties. For example, Lead Selenide or Platinum Silicide detectors may be used if longer wavelengths are desired to be measured.

In a working embodiment of the present invention, two absorption wavelength detector elements 142A, 142B and one reference wavelength detector element 142C were used. The detector elements 142 are discussed in greater detail throughout the description and it is understood that variations in the number and placement of the various detector elements 142 is within the scope of the invention of the present application. For example, an additional detector element 142 may detect temperature measurement wavelengths to estimate background radiation or sheet temperature. The use of separate wavelength detector elements, such as the detector elements 142A, 142B, 142C, enables the measuring apparatus 100 of the present application to measure the energy at corresponding wavelengths from the same sample portion of the web substantially simultaneously allowing for simultaneous detection of a plurality of characteristics of the web 102. A detector window 146 covers the opening of the detector assembly 106 and may be formed of borosilicate glass, such as Schott Borofloat 33 glass, having low absorption in the wavelengths used in the measuring apparatus 100 of the present application.

Figure 5:
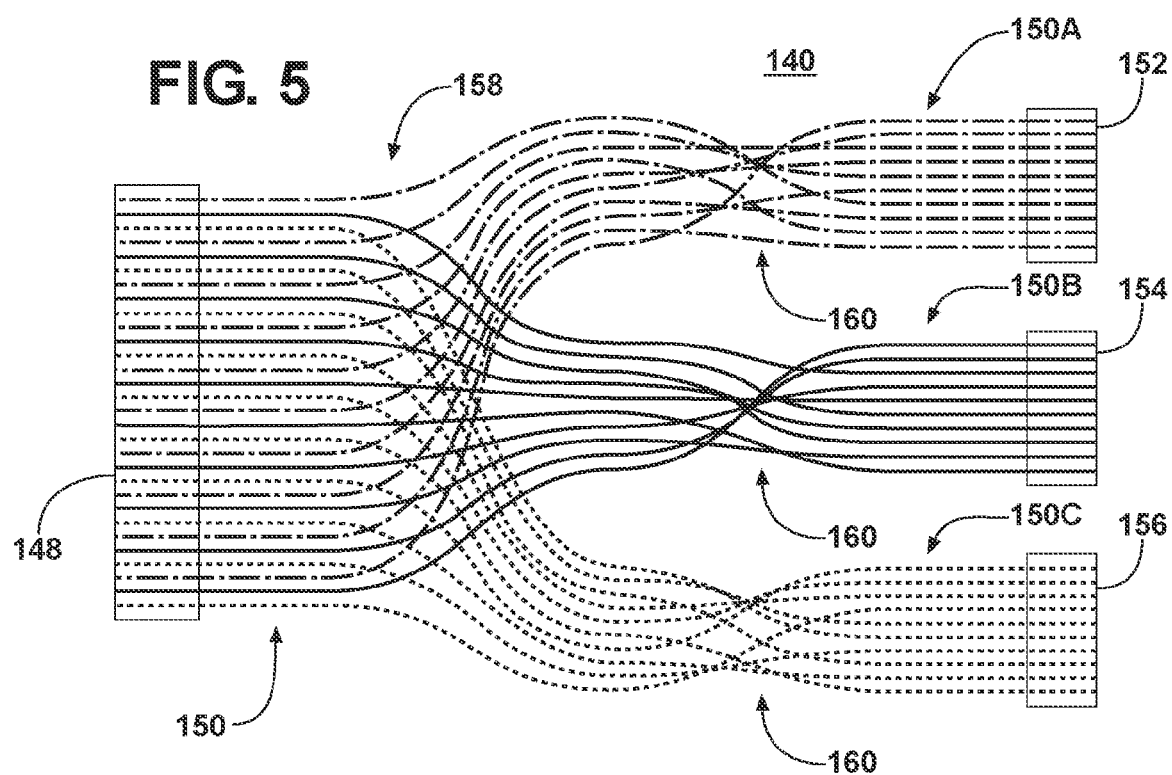

The fiber optic beam splitter 140 as shown in FIGS. 3-5 has an optical input port 148 formed as a bundle of fiber optics 150. The individual fibers are assembled into a bundle and secured, for example by epoxy, into a ferrule 148F. The tips of the fiber optics 150 in the ferrule 148F are polished to ensure that the individual fibers can efficiently receive incident light. The fiber optics 150 are individually routed inside the housing 151 to split off portions of the light received over substantially the entire surface of the input port 148 so that the light received at the optical input port 148 is distributed to a plurality of light output ports 152, 154, 156. Thus, the fiber optic beam splitter 140 defined by the fiber optics 150 serves as a light distributor.

The transmission of infrared measuring radiation through a paper web generally has large point to point intensity variations caused by small scale non-uniformity of the web 102, sometimes called "formation". When multiple detectors are used, as in the present application, either each detector must have precisely the same view of the web or the view of the web needs to be homogenized so that the field of view does not contain point to point intensity variations. Small ambiguities in the fiber optic beam splitter 140 prohibit each detector from having exactly the same view of the web. Accordingly, an effective homogenizer is required.

In the invention of the present application, the fiber optic beam splitter 140 is constructed so that in addition to light distribution, it also homogenizes the light received at the input port 148 by means of a double randomization process schematically illustrated in FIG. 5. The bundle of fiber optics 150 is finely randomized apart forming first, second and third sub-bundles of fiber optics 150A, 150B, 150C in a first randomization 158 wherein the fibers in each sub-bundle 150A, 150B, 150C are randomly selected from the fiber optics 150, i.e., from substantially the entire radiation input surface of the input port 148. Each resulting subgroup of fiber optics is also finely randomized in a second randomization 160, i.e., the fibers within each subgroup are randomly located within its corresponding light output port.

The double randomization of the fiber optics 150 can be performed in any manner that results in homogenized outputs at the light output ports 152, 154, 156. A working embodiment of the fiber optic beam splitter 140 in accordance with Applicants' specifications was obtained from Schott North America of Elmsford, N.Y. Schott provides special infrared transmitting fiber optic materials and manufactured a beam splitter 140 with a first randomization using a process proprietary to Schott identified as PD0003 and with a second randomization using a process proprietary to Schott identified as PD0002.

As shown in FIG. 3, light signals from the distributed output ports 152, 154, 156 travel through bandpass filters 162, 164, 166 and light collectors 168, 170, 172, preferably conical in shape, associated with the detector elements 142A, 142B, 142C. The bandpass filters 162, 164, 166 are tuned as closely as possible to optimize the absorption characteristics for the property each specific detector element is measuring. The beam splitter 140 is preferably adjustably mounted relative to the detectors 142 so that the distributed outputs of the fiber optics 150 may be moved closer to or farther from the bandpass filters 162, 164, 166 to thereby control the angle of light incident on the bandpass filters 162, 164, 166 by changing the solid angle of the fiber optics seen by the filters.

The signal detector elements 142A, 142B, 142C are mounted to a detector board 174 that includes circuitry 176 for processing signals generated by the detector elements 142A, 142B, 142C. The signals from the detector elements 142A, 142B, 142C are voltages that change as a function of the measured properties and the reference value. Depending on the electronics used, the signals could also be currents as should be apparent. The detector board 174 may be a printed circuit board that links to the system processor 130 and additional devices as necessary for system processing and adjustments. The detector board 174 receives a digital control message from the system processor 130. The digital control message includes gain, offset and calibration settings and performs diagnostics on the detectors 142A, 142B, 142C.

In operation, infrared light transmitted from the light source 108 irradiates a small area, hereinafter the "measured area" or single sample section, of the web 102 located between the source assembly 104 and the detector assembly 106. The material of the web 102 interacts with this incident infrared light and absorbs or transmits the various spectral components in accordance with the web properties being measured. The properties being measured may include any properties with specific and discrete infrared absorption bands, such as moisture (water), polymers, cellulose (fiber), kaolinite (clay) and the like.

As shown in FIG. 1, the detector assembly 106 is located on the side of the web 102 opposite the source assembly 104. The optical input port 148 is axially aligned with the light source 108 as indicated by a beam axis A as shown in FIGS. 1 and 3 so that the center of the input port 148 is substantially centered on the measured area of the web 102. As the web 102 moves up and down in the gap between the source assembly 104 and the detector assembly 106, the angle between the plane of the web 102 and the input port 148 changes. The angular changes may cause a wavelength dependency for energy scattered from the web 102 resulting in measurement errors that are a function of the position of the web 102 in the gap. This is usually referred to as pass-line sensitivity, or a measurement error associated with a pass-line position change of the web 102. By aligning the light source 108 and the input port 148, pass-line sensitivity is reduced.

The detector elements 142A, 142B, 142C of FIG. 3 comprise multiple extended bandgap Indium Gallium Arsenide (InGaAs) sensors. Although any size detector elements may be used in the present invention, InGaAs detector elements having a diameter of approximately one millimeter are currently preferred. The "wavelength" detector elements 142A, 142B, 142C measure infrared light over different wavelength pass bands substantially simultaneously and output corresponding voltages. Each specific pass band is selected to correspond to a spectral absorption property of a product to be measured, such as paper, plastic film or the like. As in existing sensors, the measured frequency bands are selected from the broader band of infrared light collected by tuned interference filters, the bandpass filters 162, 164, 166 in the illustrated embodiment. These tuned interference filters can be tilted to shift the center wavelength of the pass bands or the angles of light passing through them can be controlled by adjusting the reflectivity of the light collectors 168, 170, 172 or by aperturing the fiber optics. These interference filters have different absorption coefficients for light polarized in different directions.

As is well known in infrared spectroscopy, a first wavelength or desired spectral absorption wavelength is selected where absorption is high. Then a second nearby wavelength or reference wavelength is selected where absorption is low. A function of the ratio of the infrared light at these two wavelengths transmitted through a product is proportional to the weight of the property in the measured path. For water, this measurement is converted to percent moisture by dividing the measurement by the total weight of the product in that same area. In the invention of the present application, this total product weight is inferred from a function of the measured paper fiber weight. The actual absorption of infrared light is determined by the absorption of a standard unit of passage through the product and the path length of the light through the product. For example, a first InGaAs detector element is used for a fiber absorption wavelength, a second InGaAs detector element is used for a water or moisture absorption wavelength, and a third InGaAs detector element is used as a reference absorption wavelength for the fiber absorption wavelength and the moisture absorption wavelength.

Figure 6:
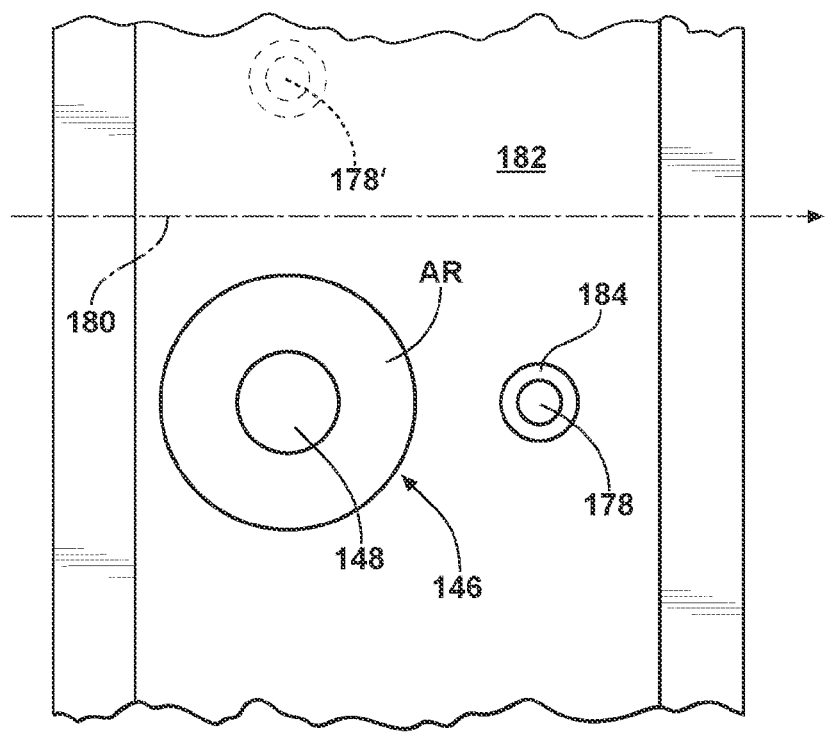
FIG. 6 is a fragmented portion of the face of the detector assembly showing placement of a pyrometer in the face.

While an additional detector element 142 may be used to detect temperature measurement wavelengths as noted earlier, it is currently preferred to use an infrared temperature sensor, such as a thermopile. Any of a variety of thermometers used for measuring temperature can be used in the invention of the present application and any such temperature sensing/measuring device will be generically referred to herein by the term "pyrometer." In the illustrated embodiment, a pyrometer 178, shown in FIGS. 1 and 6, is aligned in the machine direction (MD—into the paper as shown in FIG. 1 at 180) with but spaced from the sensor beam. A pyrometer 178', shown in FIG. 6, could also be aligned with but spaced from the sensor beam in the CD provided spatial realignment is performed during processing of the measured signals. The pyrometer 178 is connected to a face plate 182 via an insulating stand off 184. The pyrometer 178 may have a low volume air purge with air existing through the hole in the face plate 182.

Figure 7:
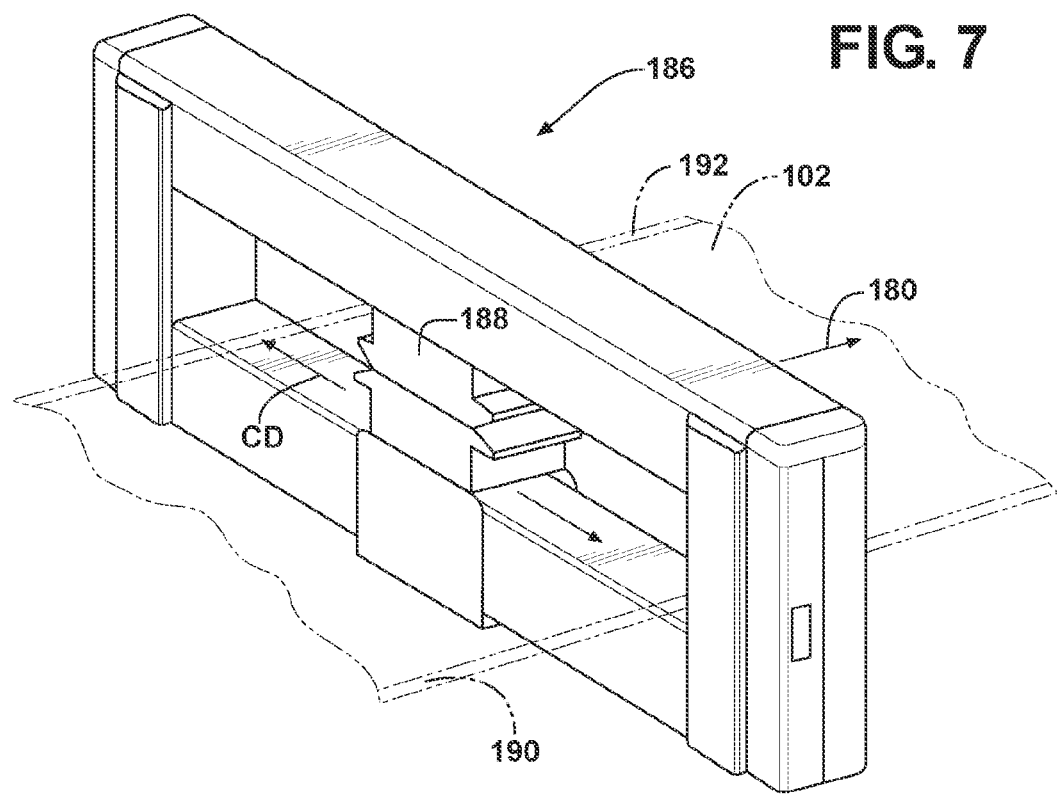
FIG. 7 illustrates a web measurement system including a scanner.

Reference is made to FIG. 7 which illustrates a web measurement system 186 including a scanner 188 which is moved back and forth in the cross machine direction (CD) across the web 102 that is being manufactured and is moving in the machine direction (MD) 180. As the scanner 188 moves across the web 102, measurement signals representative of consecutive points or small segments of the web 102, commonly referred to as "databoxes", are taken across the web 102. In the invention of the present application, the shutter system 120 is operated based on the position of a scanning head package located on the scanner 188 and including the measuring apparatus 100. During normal on-line scanning, the shutter blade 124 is retracted so that the shutter is open and the beam from the light source 108 is unblocked. However, when the scanning head package is over one of the edges 190, 192 of the web 102, the shutter blade 124 is extended so that the shutter is closed and the beam from the light source 108 is blocked.

The shutter blade 124 can be closed at each sheet edge 192, 194 as the head package stops at turnaround points, just past the first or last valid databox, so that the scanner 188 can move in the opposite direction. Alternately and currently preferred, the shutter blade 124 is closed at each $n^{th}$ sheet edge depending upon how frequently normalization is required. When the shutter is closed at one of the edges 190, 192 of the web 102, the measuring system must still be on the web 102, referred to as being "on-sheet", so that the signals from each of the detectors 142 can be measured and be representative of the web 102. The temperature at the edge (190 or 192) of the web 102 is also measured at the edge (190 or 192) of web 102 using the pyrometer 178 placed in-line with the sensor source beam in the MD in a working embodiment.

For edge measurement operations, the head package can be stopped on a sheet edge until measurement and normalization operations are complete. This mode of operation is simple and databox measurements are not missed when the scan direction reverses. However, if additional filtering is required, as may be the case in some instances, scan data can be lost during normalization and the scan period is lengthened.

Alternately, as the head package is moving away from the center of the web toward a web edge, the moment the near or far databox measurement is complete, normalization operations are started. For this mode of operation, as the head package goes past the first or last databox, stops, and then begin to accelerate back on sheet, at least a portion of the normalization tasks are run during the turn around time. In most cases, normalization tasks will not complete in time to measure the first few data boxes following scan direction reversal. In those cases, missed databoxes can be back filled with the values that were measured as the head package approached the edge of sheet.

This mode of operation has an advantage of minimizing the scan period; however, databoxes measured adjacent to a sheet edge (after a turn around) are filled with previous data. It is likely that use of these two modes will be application dependent and may be based on process characteristics (basis weight) and/or customer requirements for either faster scan period or more robust edge measurement.

Figure 8:
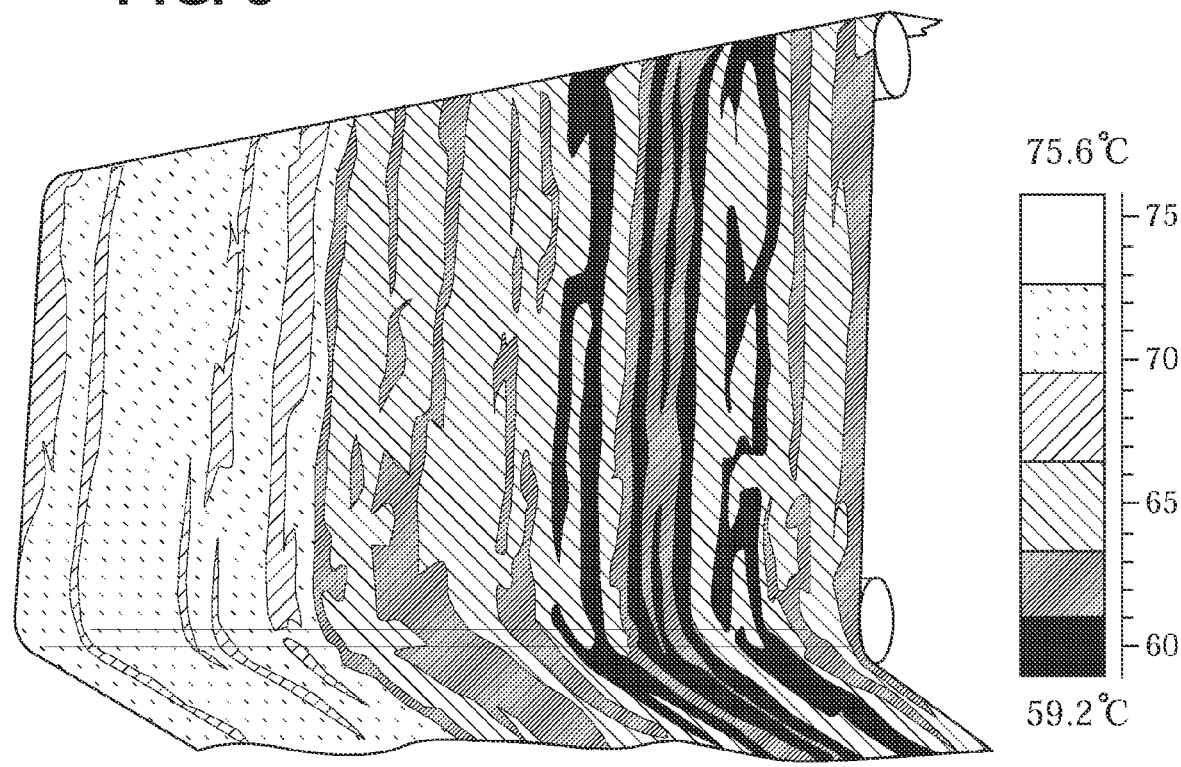
FIG. 8 illustrates temperature variations in both the cross machine direction (CD) direction and the machine direction (MD) during manufacture of a sheet of tissue paper.

In nearly all on-line paper web measurements, the web is hot due to the driers that remove water from the web and the temperature of the web varies. An example of temperature variations in both the CD and MD taken via thermography of a sheet of tissue paper being manufactured is shown in FIG. 8. The range of temperatures and variations depend on the type of paper being manufactured, the particular machine being monitored, current operating conditions, and the like.

Figure 9:
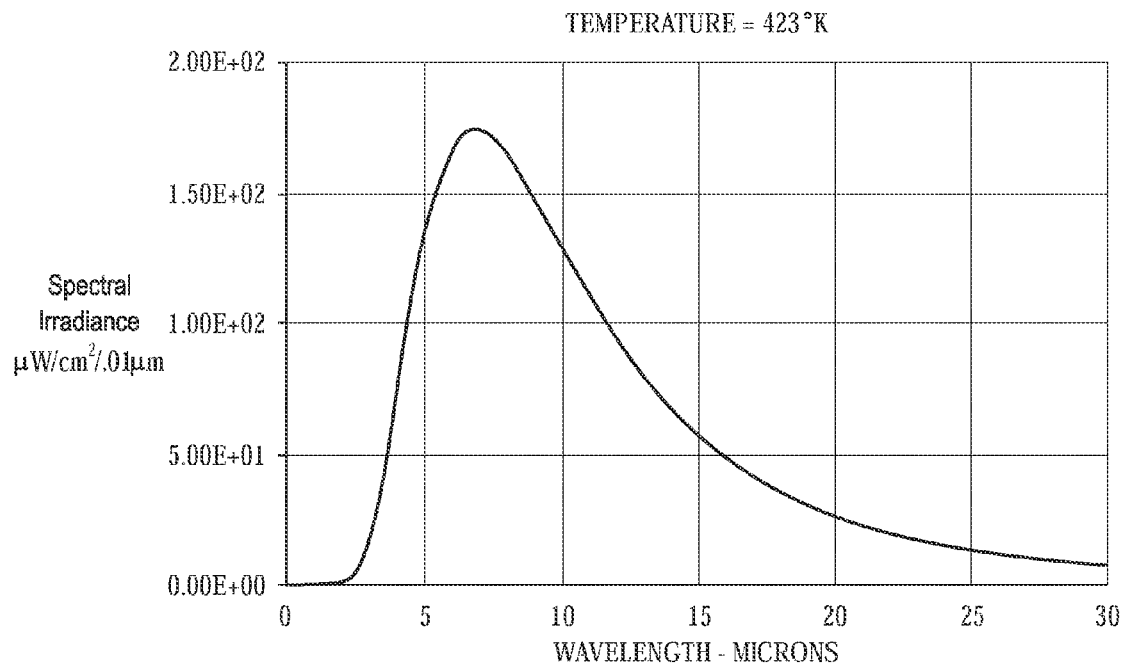
FIG. 9 illustrates wavelength dependence of Planckian radiation.
Figure 10:
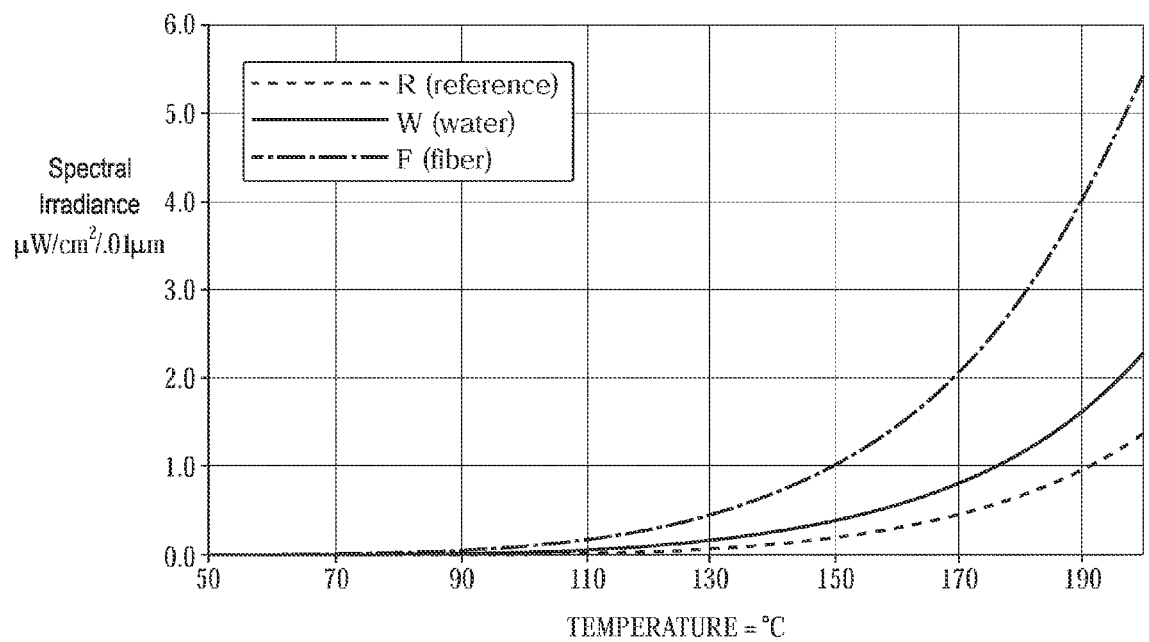
FIG. 10 illustrates Planckian radiation predictions for three wavelengths of detector elements.

Radiation from a hot sheet (Planckian radiation) is detected by each of the detector elements 142. Planckian radiation is wavelength dependent as illustrated in FIG. 9 which graphically illustrates the radiation emitted by a paper web having a temperature of about 150° C. Since Planckian radiation is wavelength dependent and each of the detector elements 142 senses a specific wavelength, the amount of Planckian radiation is different for each of the detector elements 142. Using Planck's law, the Planckian radiation predicted for the three wavelengths of the detector elements 142 (reference (R), water (W) and fiber (F)) of the illustrated embodiment of the present application, are shown in FIG. 10.

The signals generated in response to the Planckian radiation add biases that offset the signals generated in response to the radiation beam from the light source 108 after transmission through the web 102. These Planckian radiation offsets added to each signal result in errors in the computed material properties being measured. In a sensor using a full time chopper, these offsets are removed by measuring the Planckian radiation during the shutter closed times. In the present application, the Planckian radiation offsets are removed using the sheet temperature and the detector element measurements made while the shutter is closed at one of the edges 190, 192 of the web 102. More particularly, as the scanner 188 scans the web 102, the pyrometer 178 measures the temperature of each databox across the web 102 and a Planckian correction factor is generated for each databox based on the difference between the edge of sheet temperature and the databox temperature.

The Planckian radiation detected by each detector 142 is affected by at least the optical throughput of each sub-bundle of fiber optics 150A, 150B, 150C of the fiber optic beam splitter 140; the absorption characteristics of the fiber optics 150; the transmission factors of the band pass filters 162, 164, 166; differences in electronic gains of the circuitry 176; and, the wavelength dependent response of each detector 142. These effects result in gain differences between the detecting channels, three channels that correspond to the detector elements 142A, 142B and 142C in the illustrated embodiment. These channel differences produce differences between the measured Planckian radiation signals and the signals predicted by the Planckian radiation law shown in FIG. 10.

For calibration of the throughput of the sensor optical subassembly shown in FIG. 3 during manufacturing, Planckian signals are measured at high measurement amplifier gains while the optical input port 148 is directed toward a hot black plate representative of a theoretical blackbody. The temperature of the black plate is accurately measured and the deviation between a theoretical Planckian radiator and the actual measured signal in each channel is measured. A single scale factor or throughput head constant is found for each channel to make the detected signal equal to the ideal signal. The scale factors not only correct for differences in the optical path but also convert the output units from $\mu W/cm^2/0.01 \ \mu m$ to a voltage level.

Figure 11:
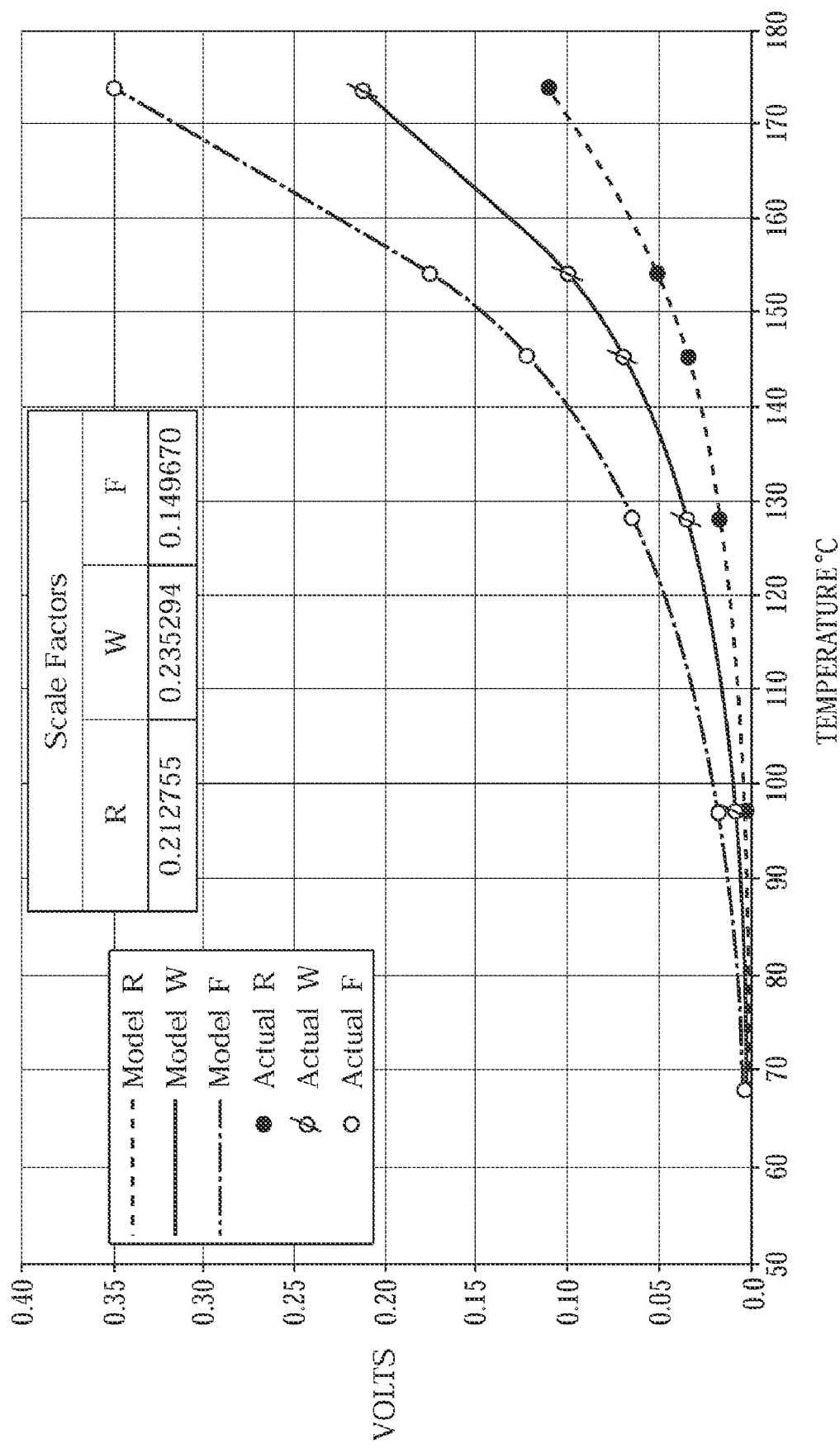
FIG. 11 illustrates examples of derived scale factors versus ideal radiation estimates.

An example of derived scale factors versus ideal radiation is shown in FIG. 11 with the calibration scale factors shown at the top of the figure wherein data were measured and corrected at a measurement amplifier gain of $2^{13}$. The online measurement may be made at different gain settings with the actual amplifier gain for each step being know within reasonable accuracy, either by a calibration step during sensor standardize or by electronic design. In a working embodiment, 16 gains steps ranging from $2^0$ to $2^{15}$ are available. Therefore, at any known sensor gain step, the influence of Planckian radiation may be calculated at any measured sheet temperature.

The voltage values measured at each $n^{th}$ edge of sheet are composed of both Planckian radiation and electronic offset drift. Experience has shown that electronic offset drift is relatively slow, however (as shown in FIG. 8) Planckian radiation may change rapidly. The rate of change of electronic offset drift determines how often the edge of sheet chop is made.

The inventors of the present application have determined that the predictions of Planck's law correlate well with laboratory measurements. For the infrared measuring of the present application, Planck's equation only needs to be scaled to sensor voltage responses to background radiation at a known temperature for on-line correction. The scaled Planckian correction functions are defined for the reference (R), moisture (W) and fiber (F) measurement channels as follows:

$$R\_planck(T) = S_R \frac{U}{\lambda_R^5}\left(\exp\left(\frac{V}{(T+273.15)\lambda_R}\right)-1\right)^{-1}$$

$$W\_planck(T) = S_W \frac{U}{\lambda_W^5}\left(\exp\left(\frac{V}{(T+273.15)\lambda_W}\right)-1\right)^{-1}$$

$$F\_planck(T) = S_F \frac{U}{\lambda_F^5}\left(\exp\left(\frac{V}{(T+273.15)\lambda_F}\right)-1\right)^{-1}$$

Where U and V are coefficients used to simplify the form of Planck's equation:
$U=2hc^2$ where h is Planck's constant and c is the speed of light;
$V=hc/k$ where k is Boltzmann's constant,
$\lambda_R$ is the reference signal wavelength, $\lambda_w$ is the water signal wavelength, $\lambda_F$ is the cellulose signal wavelength and T is the web temperature in degrees Centigrade. $S_R$, $S_W$ and $S_F$ are channel scaling factors as discussed above with reference to FIG. 11 used to convert the theoretical spectral irradiance (a function of sheet temperature and signal wavelength) to sensor voltage responses at a gain of $2^{13}$. Accordingly, calculations using these functions are in units of volts at a gain level of $2^{13}$, an arbitrary gain level from which the Planckian correction voltages are defined. These functions are the basis of the Planckian corrections.

These Planckian correction functions are used to estimate the change in background radiation signal, the Planckian radiation offset, based on the change in sheet temperature since the most recent edge of scan measurement or baseline normalization (BN). The change in sheet temperature is, therefore, the difference between the temperature of the current databox, T_box, and the temperature measured at the most recent baseline normalization T_BN.

Planckian correction estimates (dR_planck, dW_planck and dF_planck) are computed using the scaled Planckian correction functions for each temperature, subtracting the result and adjusting the result to the current gain setting N. These corrections take the following mathematical form:

$$dR\_planck(T\_box,T\_BN,N)=(R\_planck(T\_box)-R\_planck(T\_BN))\cdot 2^{(N-13)}$$

$$dW\_planck(T\_box,T\_BN,N)=(W\_planck(T\_box)-W\_planck(T\_BN))\cdot 2^{(N-13)}$$

$$dF\_planck(T\_box,T\_BN,N)=(F\_planck(T\_box)-F\_planck(T\_BN))\cdot 2^{(N-13)}$$

During on-line scanning, each measurement signal is averaged into a databox: R_box, W_box, F_box and T_box. Signal offsets are removed from the wavelength channels in two stages. First, the electronic drift offset values determined at the most recent baseline normalization are subtracted. Second, the Planckian correction estimates are then subtracted.

$$R=R\_box-R\_BN-dR\_Planck(T\_box,T\_BN,N)$$

$$M\_w=(W\_box-W\_BN)\cdot GW(N)-dW\_Planck(T\_box,T\_BN,N)$$

$$M\_f=(F\_box-F\_BN)\cdot GF(N)-dF\_Planck(T\_box,T\_BN,N)$$

In the case of the water and fiber channels, this result is gain normalized based on the most recent gain normalization data and the current gain of the sensor, N. These signals, R, M_w and M_f, are used as the raw input data for determination of accurate measurements substantially free of electronic drift offset and Planckian offset.

The above description has been directed to operation of a scanning head package that is scanned in the CD across a web moving in the MD and includes performing chops at every edge or every $n^{th}$ edge of the web. While edge chopping during scanning operation is performed the majority of the time since it corresponds to usual machine operation for web production, the measuring system of the present application also enables the derivation of correction factors during operation in a single point and other possible machine operating modes.

In a first exemplary single point operating mode, the scanner is stopped at a specific CD point for the time needed to accumulate sufficient data for a required operation. Examples of operation in this single point operating mode include the collection of data to detect the source of unusual behavior in a web making machine, to tune response times to CD actuators, to detect wet or dry problems near the edge of sheet and the like. While times in this single point mode can vary, an exemplary range could be from one hour to one day. In a second exemplary single point mode, referred to as calibrate sample mode, the scanner is again stopped at a specific CD point; however, usually the CD point is monitored for a shorter time, such as ten minutes. The calibrate sample mode can be used, for example, to create a printed report of sensor readings at a selected single CD point that is usually where a calibration sample is likely to be cut from the paper reel after production.

Non-scanning operation of the measuring system of the present application is substantially the same as discussed above for scanning operation except for the timing of the chop. During non-scanning operation, since the measuring system is located at a single CD point, chopping operations are not made to coincide with an edge of sheet but rather, chopping operations are performed based on elapsed time periods. Overall, the chop time, i.e., the time that the shutter blocks the light source, is about the same as during scanning measurements, only the place on the sheet where the chop is made is different. That is, chops are made at the specific CD point on the web and correction factors, including Planckian correction, are produced the same as described above.

Non-scanning operation enables use of the invention of the present application in measurement systems that do not scan. For example, a measurement system 200 may be constructed using an array 202 of fixed sensors extending across the entire web 204 as shown in FIG. 12. The array 202 of fixed sensors includes infrared sensors 142 and can also include pyrometers. Preferably, infrared sensors and a pyrometer, if used, in the array 202 of sensors would be provided for each databox across the web 204. A light source 206 can be provided for light to be transmitted through the web 204 as in the measuring apparatus 100 of FIG. 1. Alternately or in combination with the light source 206, a light source 208 can be used if illumination is to be provided on the same side of the web 204 as the sensor array 202 in the measurement system 200.

The light sources 206, 208 are illustrated as single, distributed light sources although other light sources can also be used in the measurement system 200. The light sources 206, 208 can be turned off for light chopping operations. Alternately, the light sources 206, 208 can be formed as a light pipe with a slot for illuminating the web 204. The light pipe can be rotated to cut off the light forming a rotating shutter for a long distributed source. A light pipe could be constructed to cut off only a portion of the light source, say portions at each edge, if desired. As will be apparent to those skilled in the art, chopping a distributed source can be performed in a number of ways.

Although the invention has been described with particular reference to certain illustrated embodiments thereof, variations and modifications of the present invention can be effected within the spirit and scope of the following claims.

What is claimed is:

1. A method for measuring at least one property of a web of material as said web is being manufactured and is moving in a machine direction (MD) by scanning measurement apparatus back and forth across said web in a cross-machine direction (CD), said measuring apparatus comprising a source of radiation appropriate for measuring said at least one property that is directed toward said web and at least first and second sensors that receive measuring radiation from said web, said method comprising:
receiving radiation representative of said at least one property of said web at consecutive points across said web;
measuring temperature at said consecutive points across said web;
interrupting said measuring radiation at an edge of said web;
sensing radiation at said edge of said web while said measuring radiation is interrupted;
measuring temperature of said edge of said web;
developing correction factors for said at least one property from said web edge temperature and the measured temperatures of said consecutive points for each of said consecutive points across said web; and
applying said correction factors at each of said consecutive points across said web to correct for Planckian radiation contained in radiation representative of said at least one property of said web received at said consecutive points across said web.

2. The method as claimed in claim 1 wherein interrupting said measuring radiation at an edge of said web comprises interrupting said measuring radiation at every $n^{th}$ edge of said web.

3. The method as claimed in claim 1 wherein developing correction factors comprises developing correction factors in the form of voltage levels.

4. The method as claimed in claim 3 wherein developing correction factors in the form of voltage levels comprises solving the equation:

$$\chi\_\text{planck}(T) = S_\chi \frac{U}{\lambda_\chi^5} \left( \exp\left( \frac{V}{(T+273.15)\lambda_\chi} \right) - 1 \right)^{-1}$$

Where:
$\chi$=at least one property;
$U=2hc^2$;
$V=hc/k$;
$\lambda_\chi$=at least one property wavelength;
$T$=web temperature in degrees Centigrade; and
$S_\chi$=throughput head constant for property.

5. The method as claimed in claim 1 wherein receiving radiation representative of said at least one property of said web at consecutive points across said web further comprises:
splitting said radiation representative of said at least one property of said web into at least first and second portions; and
distributing said at least first and second portions to said at least first and second sensors.

6. The method as claimed in claim 5 wherein splitting said radiation representative of said at least one property of said web and distributing said as least first and second portions to said at least first and second sensors is performed by beam splitting apparatus and further comprises homogenizing said radiation.

7. The method as claimed in claim 6 wherein homogenizing said radiation is performed by said beam splitting apparatus which comprises a bundle of fiber optics and comprises:
   randomly selecting ones of said fiber optics from substantially an entire radiation input surface of an input port of said beam splitting apparatus;
   individually routing said randomly selected ones of said fiber optics to form at least first and second sub-bundles of fiber optics corresponding to said first and second portions of said radiation; and
   randomly distributing fiber optics of said at least first and second sub-bundles over at least first and second output ports of said beam splitting apparatus.

8. Measurement apparatus for measuring at least one property of a web of material as said web is being manufactured and is moving in a machine direction (MD) by scanning said measurement apparatus back and forth across said web in a cross-machine direction (CD), said apparatus comprising:
   a source of measuring radiation appropriate for measuring said at least one property, said measuring radiation being directed toward said web;
   at least first and second sensors that receive radiation from said web and generate signals representative of said radiation;
   at least one pyrometer that measures temperature of said web; and
   a shutter mechanism that interrupts said source of measuring radiation when said sensor is positioned on an edge of said web wherein said sensor generates signals in response to measuring radiation representative of said at least one property and Planckian radiation when said source of measuring radiation is uninterrupted for each of consecutive points extending across said web between edges of said web and said sensor generates signals in response to Planckian radiation for at least one of said edges of said web while said source of measuring radiation is interrupted, and said pyrometer measures a temperature for each of said consecutive points extending across said web and for at least one of said edges of said web; and
   a controller that develops correction factors for said at least one property for each of said consecutive points across said web from a measured edge temperature and the measured temperatures of each of said consecutive points across said web, and applies said correction factors for each of said consecutive points across said web to correct for Planckian radiation contained in radiation sensed for each of said consecutive points across said web.

9. Measuring apparatus as claimed in claim 8 wherein said source of measuring radiation is on a first side of said web and said sensor is on a second side of said web opposite to said first side.

10. Measuring apparatus as claimed in claim 8 wherein said at least one pyrometer comprises a single pyrometer that is aligned with said source of measuring radiation in a machine direction (MD) but offset in a cross machine direction (CD).

11. Measuring apparatus as claimed in claim 10 wherein said source of measuring radiation is on a first side of said web and said sensor and pyrometer are on a second side of said web opposite to said first side.

12. Measuring apparatus as claimed in claim 8 wherein said at least one pyrometer comprises a single pyrometer that is aligned with said source of measuring radiation in a cross machine direction (CD) but offset in a machine direction (MD) and said controller applies spatial realignment during development of said correction factors.

13. Measuring apparatus as claimed in claim 12 wherein said source of measuring radiation is on a first side of said web and said sensor and pyrometer are on a second side of said web opposite to said first side.

14. Measurement apparatus for measuring at least one property of a web of material as said web is being manufactured and is moving in a machine direction (MD) by scanning said measurement apparatus back and forth across said web in a cross-machine direction (CD), said apparatus comprising:
   a source of measuring radiation appropriate for measuring said at least one property, said measuring radiation being directed toward a first side of said web;
   beam splitting apparatus that receives radiation from a second side of said web opposite to said first side, said beam splitting apparatus having a radiation input port directed toward an area of said web irradiated by said measuring radiation and at least a first output port and a second output port;
   a first sensor that receives radiation from said first output port of said beam splitting apparatus and generates signals representative of received radiation;
   a second sensor that receives radiation from said second output port of said beam splitting apparatus and generates signals representative of received radiation;
   a pyrometer that measures a temperature of said web; and
   a shutter mechanism that interrupts said source of measuring radiation when said sensor is positioned on an edge of said web wherein said first and second sensors generate signals in response to measuring radiation and Planckian radiation when said source of measuring radiation is uninterrupted for each of consecutive points extending across said web between edges of said web and said first and second sensors generate signals in response to Planckian radiation for at least one of said edges of said web while said source of measuring radiation is interrupted, and said pyrometer measures a temperature for each of said consecutive points extending across said web and for at least one of said edges of said web; and
   a controller that develops correction factors for said at least one property for each of said consecutive points across said web from a measured edge temperature and measured temperatures of each of said consecutive points across said web, and applies said correction factors for each of said consecutive points across said web to correct for Planckian radiation contained in radiation sensed for each of said consecutive points extending across said web between said edges of said web.

15. Measuring apparatus as claimed in claim 14 wherein said radiation input port of said beam splitting apparatus is aligned with said source of measuring radiation and homogenizes received radiation as said received radiation passes through said beam splitting apparatus.

16. Measuring apparatus as claimed in claim 15 wherein said radiation input port of said beam splitting apparatus comprises a bundle of fiber optics, ones of said fiber optics being selected randomly from said bundle of fiber optics defining said input port and individually routed to form at least first and second sub-bundles of fiber optics which split off portions of radiation received over substantially the entire surface of said input port to said at least first and second output ports, fiber optics of said at least first and second sub-bundles being randomly distributed over at least said first and second output ports.

17. A method for measuring at least one property of a web of material as said web is being manufactured and is moving in a machine direction (MD), said measuring apparatus comprising a source of radiation appropriate for measuring said at least one property that is directed toward said web and at least first and second sensors that receive measuring radiation from said web, said method comprising:
- receiving radiation representative of said at least one property of said web from at least one point in the cross direction (CD) of said web;
- measuring temperature at said at least one point in the CD of said web;
- interrupting said measuring radiation;
- sensing radiation received from said web while said measuring radiation is interrupted;
- measuring temperature of said web while said measuring radiation is interrupted;
- developing correction factors for said at least one property from said temperature measured while said measuring radiation is interrupted and the measured temperatures of said at least one point of said web; and
- applying said correction factors at said at least one point of said web to correct for Planckian radiation contained in radiation representative of said at least one property of said web received at said at least one point of said web.

18. The method as claimed in claim 17 wherein interrupting said measuring radiation comprises interrupting said measuring radiation after elapsed time periods.

19. A method for measuring at least one property of a web of material as said web is being manufactured and is moving in a machine direction (MD) by scanning measuring apparatus back and forth across said web in a cross-machine direction (CD), said measuring apparatus comprising a source of radiation appropriate for measuring said at least one property that is directed toward said web and at least first and second sensors that receive measuring radiation from said web, said method comprising:
- receiving radiation representative of said at least one property of said web at consecutive points across said web;
- measuring temperature at said consecutive points across said web;
- interrupting said measuring radiation at at least one of said consecutive points across said web;
- sensing radiation received from said web at said at least one of said consecutive points across said web while said measuring radiation is interrupted;
- measuring temperature at said at least one of said consecutive points across said web while said measuring radiation is interrupted;
- developing correction factors for said at least one property from said temperature measured at said at least one of said consecutive points across said web while said measuring radiation is interrupted and the measured temperatures of said consecutive points for each of said consecutive points across said web; and
- applying said correction factors at said consecutive points across said web to correct for Planckian radiation contained in radiation representative of said at least one property of said web received at said consecutive points across said web.

* * * * *

UNITED STATES PATENT AND TRADEMARK OFFICE
CERTIFICATE OF CORRECTION

PATENT NO. : 8,148,690 B2
APPLICATION NO. : 12/566180
DATED : April 3, 2012
INVENTOR(S) : Sturm et al.

It is certified that error appears in the above-identified patent and that said Letters Patent is hereby corrected as shown below:

Col. 11, line 47, "each step being know within reasonable accuracy" should read -- each step being known within reasonable accuracy --;

Col. 14, line 67, "distributing said as least first" should read -- distributing said at least first --;

Col. 17, lines 12-13, "one point in the cross direction (CD)" should read -- one point in the cross-machine direction (CD) --.

Signed and Sealed this
Nineteenth Day of March, 2013

Teresa Stanek Rea
*Acting Director of the United States Patent and Trademark Office*